(12) United States Patent
Mukai et al.

(10) Patent No.: US 7,758,317 B2
(45) Date of Patent: Jul. 20, 2010

(54) METHOD OF ANALYZING VAPORIZATION PATTERN OF SOLVENT AND SOLVENT VACUUM VAPORIZATION DEVICE

(75) Inventors: Koji Mukai, Tokyo (JP); Fujio Ito, Tokyo (JP); Satoru Takahashi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 1075 days.

(21) Appl. No.: 10/571,122

(22) PCT Filed: Sep. 8, 2004

(86) PCT No.: PCT/JP2004/013039

§ 371 (c)(1),
(2), (4) Date: Mar. 9, 2006

(87) PCT Pub. No.: WO2005/026717

PCT Pub. Date: Mar. 24, 2005

(65) Prior Publication Data

US 2006/0288604 A1    Dec. 28, 2006

(30) Foreign Application Priority Data

Sep. 10, 2003    (JP)    ............... 2003-318164

(51) Int. Cl.
*F04B 3/00*    (2006.01)
*F04B 5/00*    (2006.01)

(52) U.S. Cl. ............ 417/251; 417/2; 417/307; 417/252; 417/304; 417/441; 422/83; 73/863.23

(58) Field of Classification Search ............ None
See application file for complete search history.

(56) References Cited

U.S. PATENT DOCUMENTS 3,618,363 A    11/1971    Kraus 3,847,554 A    11/1974    Su
4,764,344 A    8/1988    Knab
4,984,974 A *    1/1991    Naya et al. ............ 418/87
5,712,421 A    1/1998    Raisanen
7,028,562 B2 *    4/2006    LaCourse et al. ........ 73/863.23

FOREIGN PATENT DOCUMENTS

DE    3710782    * 10/1988

(Continued)

OTHER PUBLICATIONS am Ende et al. 2000, Organic Process Research and Development, 4, 587-593.*

(Continued)

*Primary Examiner*—Jill Warden
*Assistant Examiner*—Sally A Sakelaris
(74) *Attorney, Agent, or Firm*—Oblon, Spivak, McClelland, Maier & Neustadt, L.L.P.

(57)    ABSTRACT

A method for analysis of solvent evaporation patterns includes: continuously evacuating the gas of a single-component or multicomponent solvent evaporated under desired evaporation conditions from an object containing the single-component or multicomponent solvent housed in an airtight container, with evacuation means from the airtight container to an exhaust path connected to an exhaust port of the evacuation means; sampling a gas at predetermined time intervals from a desired point between the airtight container and the outlet of the exhaust path with the continuous evacuation maintained; measuring the solvent gas contained in the sampled gas; and determining an evaporation pattern of the solvent from the object under the desired evaporation conditions, from results of the measurement.

8 Claims, 6 Drawing Sheets

FOREIGN PATENT DOCUMENTS

| | | |
|---|---|---|
| JP | 54-126599 | 10/1979 |
| JP | 2-115765 | 4/1990 |
| JP | 3-284651 | 12/1991 |
| JP | 4-131736 | 5/1992 |
| JP | 6-87802 | 3/1994 |
| JP | 2000-80072 | 3/2000 |
| JP | 2003-14721 | 1/2003 |

OTHER PUBLICATIONS

Organic Process Research and Development 2000 587-593.*

Vacuubrand Product Manual, Lachenmann et al. Publicly available: 1992.* am Ende, David J.,"On-Line Monitoring of Vacuum Drayers Using Mass Spectrmetry", Organic Process Research & Development, vol. 4, No. 6, pp. 587-593, 2000.

* cited by examiner

METHOD OF ANALYZING VAPORIZATION PATTERN OF SOLVENT AND SOLVENT VACUUM VAPORIZATION DEVICE

TECHNICAL FIELD

The present invention relates to a method for analyzing the evaporation patterns of solvents and to a vacuum solvent evaporator.

BACKGROUND ART

Chemical substances for medical drugs or the like are produced by synthesizing the substances in solvents or extracting them to solvents and removing the unnecessary solvents by evaporation. The solvents, if necessary, may be completely evaporated so that the substances are crystallized, that is, dried (see, for example, Patent Documents 1 and 2).

The solvent used for producing a chemical substance is appropriately selected depending on the chemical substance desired, and the optimal conditions (treatment temperature, evaporation rate, treatment time, etc.) for evaporation of the solvent are varied depending of the chemical substance.

Before the industrial production of such a chemical substance, in general, the optimal evaporation conditions being predetermined from investigation for the evaporation pattern of the solvent and the state of the resulting chemical substance, under different evaporation conditions determined by varying the treatment temperature, the evaporation rate of the solvent, the treatment time, the degree of vacuum, and other conditions, using laboratory equipment, the chemical substance was produced.

One of the conventional techniques for determining the optimal evaporation conditions according to object containing a single-component solvent is a mass measurement technique in which the evaporation rate of the solvent is measured by measuring the changes in mass of the object on a balance with elapsed time. If the object contains several types of solvent, a break technique is employed for the determination of the evaporation rate of the solvent. In the break technique, the solvents in an object are evaporated and removed by evacuating an airtight container, such as a model of dryer, containing the object with a vacuum pump. In the course of this process, the vacuum pump is suspended several times so that the pressure in the airtight container returns to atmospheric pressure, and part of the object in the airtight container is sampled and weighed on a balance at each time. The sample is dissolved in an appropriate solvent, and the content of each residual solvent is measured by gas chromatography. Then, the object is vacuum-dried again. This procedure is repeated, and the latest measurement results are compared with the previously obtained measurement results. The evaporation rate of each solvent is obtained from the difference between the contents.

Patent Document 1: Japanese Unexamined Patent Application Publication No. 2000-80072

Patent Document 2: Japanese Unexamined Patent Application Publication 6-87802

DISCLOSURE OF INVENTION

Problems to be Solved by the Invention

The mass measurement technique however is useful only for objects containing a single-component solvent, and measures only the total mass of solvents for a multicomponent system containing plural types of solvents. In addition, if an apparatus operates, the balance or the like is swung. This makes the measurement difficult. Accordingly, the vacuum pump, dryer, evaporator, and other apparatuses must be suspended for a while. This is waste of time.

On the other hand, the break technique can measure multicomponent solvents. In this technique, however, the vacuum state must be broken to return to atmospheric pressure for sampling. Consequently, it takes time to reduce the pressure to a predetermined vacuum pressure, and it is difficult to know when the pressure reaches the predetermined vacuum pressure or when the measurement is restarted. Furthermore, the break disturbs the evaporation system, so that, for example, the content of the residual solvent and the evaporation rate are likely to vary. In order to minimize the disturbance of the system, few points can be measured. Thus, it is difficult to accurately know effects on the evaporation conditions (evaporation rate, effective exhaust rate, overall heat transfer coefficient, detection of evaporation of a trace amount of solvent, etc.) and to determine optimal evaporation conditions.

In view of the above circumstances, the object of the present invention is to provide a method for easily and accurately analyzing evaporation patterns of, for example, a multicomponent solvent under respective evaporation conditions so as to determine the optimal evaporation conditions, and a vacuum solvent evaporator capable of embodying the method.

MEANS FOR SOLVING THE PROBLEMS

In order to accomplish the above object, the present invention provides a method for analysis of solvent evaporation patterns which includes continuously evacuating a gas of a single-component or multicomponent solvent evaporated under desired evaporation conditions from an object containing the single-component or multicomponent solvent housed in an airtight container, with evacuation means from the airtight container to an exhaust path connected to an exhaust port of the evacuation means; sampling the gas at predetermined time intervals from a desired point between the airtight container and the outlet of the exhaust path with holding the continuous evacuation conditions; measuring the solvent gas contained in the sampled gas; and determining an evaporation pattern of the solvent from the object under the desired evaporation conditions, from results of the measurement.

In the method for analysis of solvent evaporation patterns of the present invention, the evacuation means may be, for example, an aspirator, a pressure reducing pump, or a vacuum pump. If evaporation in a practical process is performed under conditions close to a vacuum, a vacuum pump is preferably used.

In the method for analysis of solvent evaporation patterns of the present invention, preferably, an inert gas is supplied to the path from the airtight container to the exhaust port of the vacuum pump to dilute the solvent gas while the flow rate of the inert gas is measured, and the diluted solvent gas is discharged to the exhaust path. More preferably, the inert gas is supplied into an internal exhaust path of the vacuum pump, that is, between the suction port and exhaust port of the vacuum pump.

If a vacuum pump is used as the evacuation means, gas is preferably sampled from the exhaust port of the vacuum pump.

In the method for analysis of solvent evaporation patterns of the present invention, how the sample gas is measured is not particularly limited. For example, gas chromatography, colorimetry, mass spectrometry, or infrared spectroscopy may be employed. Among these preferred is gas chromatography.

In the method for analysis of solvent evaporation patterns of the present invention, preferably, the evaporation pattern of the solvent from the object is determined from the concentration of the solvent gas calculated from the results of the measurement by gas chromatography, the dilution ratio of the inert gas, and the flow rate of the inert gas. The temperature of the object in the airtight container and the internal pressure of the airtight container may be added to the data of the analysis, if necessary.

The vacuum solvent evaporator for an object to be treated according to the present invention includes an airtight container for housing an object containing a single-component or multicomponent solvent; evacuation means for evacuating a gas of the solvent evaporated in the airtight container, from the airtight container; and measuring means for measuring the solvent gas sampled from the gas evacuated while a continuous evacuation state produced by the evacuation means is maintained.

Preferably, the vacuum solvent evaporator includes an airtight container for housing an object containing a single-component or multicomponent solvent; a vacuum pump including a suction port from which a gas of the solvent evaporated in the airtight container is drawn, an exhaust port from which the gas is discharged, and an inert gas supply port through which an inert gas is supplied from the outside to the solvent gas drawn into the vacuum pump; inert gas supply means for supplying the inert gas into the vacuum pump through the inert gas supply port while the amount of gas supply is measured, thereby diluting the drawn solvent gas; inert gas supply amount storage means for storing the amount of inert gas supply measured by the inert gas supply means; a gas chromatograph for automatically sampling the gas discharged from the exhaust port of the vacuum pump at predetermined time intervals and measuring the solvent gas in the sampled gas; arithmetic operation means for calculating the concentration of the solvent gas from the measurement results of the gas chromatograph and a previously prepared calibration curve; and concentration data storage means for storing the solvent gas concentration obtained by the arithmetic operation means.

In the present invention, the vacuum pump is not particularly limited, but a preferred vacuum pump is, for example, of a dry type. Exemplary dry vacuum pumps include dry diaphragm vacuum pumps, dry rotary (vane) vacuum pumps, dry scroll vacuum pumps, oil-free reciprocating plunger vacuum pumps, and dry screw vacuum pumps. Preferably, a dry diaphragm vacuum pump or a dry screw vacuum pump is used.

In the present invention, how the inert gas is supplied to the internal exhaust path of the vacuum pump is not particularly limited. For example, the vacuum pump may be provided with a gas ballast mechanism (gas ballast valve) through which the inert gas is supplied (see PCT Japanese Translation Patent Publication No. 2003-518228), or the vacuum pump may be provided with a through hole passing through its casing to the inside and the inert gas is supplied through the through hole (see Japanese Unexamined Patent Application Publication No. 11-294357).

The dry diaphragm vacuum pump including the gas ballast mechanism may be commercially available (for example, from Vacuubrand). Preferably, such a vacuum pump includes at least four diaphragm pump chambers connected in series, each having a diaphragm pump chamber inlet through which gas is drawn and a diaphragm pump outlet from which the gas is discharged, and the gas ballast mechanism is disposed between the outlet of the third or posterior diaphragm pump chamber upstream from the last diaphragm pump chamber and the inlet of the following diaphragm pump chamber. The number of the diaphragm pump chambers is preferably 8 or less. As the number of the diaphragm pump chambers increases, the ultimate pressure is reduced (becomes higher vacuum), but the solvent gas becomes liable to condense in diaphragm pump chambers anterior to the inert gas supply port.

The evaporation in the present invention includes a unit operation of drying. The vacuum evaporation can be performed not only while the object is being heated as in heat drying, but also while the object is in a frozen state as in vacuum-freeze drying, or in room temperature.

The solvents used in the present invention include organic solvents, such as acetone, dichloromethane, and isopropyl alcohol (IPA), and water. The evaporation conditions include treating temperature at which the object is treated, pressure in the airtight container, exhaust rate of vacuum pump, treating time, etc.

The evaporation pattern mentioned in the present invention refers to, for example, the changes with time in evaporation rate of a specific solvent evaporating from the object or the changes with time in vapor concentration of the solvent gas, in evaporation at an arbitrary temperature and an arbitrary exhaust rate of vacuum pump.

The inert gas used in the present invention is not particularly limited as long as it is inert to the solvent to be measured. Examples of the inert gas include argon gas, helium gas, carbon dioxide gas, and nitrogen gas, and nitrogen gas is preferred from the economical point of view.

Preferably, the vacuum solvent evaporator of the present invention further includes temperature control means for controlling the temperature of the object to be treated in the airtight container, such as a heating device or a cooling device, a temperature sensor for measuring the temperature of the object in the airtight container, and a pressure sensor for measuring the pressure in the airtight container.

ADVANTAGEOUS EFFECT OF THE INVENTION

In the method for analysis of solvent evaporation patterns of the present invention, the gas of a single-component or multicomponent solvent evaporated from an object containing the single-component or multicomponent solvent housed in an airtight container under desired evaporation conditions is continuously evacuated, with evacuation means from the airtight container to an exhaust path connected to an exhaust port of the evacuation means, and a gas is sampled at predetermined time intervals from a desired point between the airtight container and the outlet of the exhaust path with the continuous evacuation maintained. The solvent gas contained in the sampled gas is measured, and an evaporation pattern of the solvent from the object under the desired evaporation conditions is determined from results of the measurement. Since sampling can be performed while evacuation is continued without breaking a vacuum, unlike the known methods, the pressure is stable and is not affected even by frequent sampling. Since the step of restoring the evacuation state is not necessary after sampling, unlike the known methods, the work time can be short. Also, the number of samplings can be increased without changing the work time. Thus, accurate and detailed data can be obtained in a short time.

Since the data is accurate and in detail, how the evaporation conditions affect the state of the object dried can be accurately known. Thus, optimal conditions for manufacture can be easily set.

More detailed drying rate curve of a particular object to be dried (hydrate crystals or the like) can be automatically calculated and, thus, various new findings can be obtained.

The use of a vacuum pump as the evacuation means allows evaporation under conditions close to a vacuum. A dry vacuum pump ensures the delivery of the solvent to the exhaust path without dissolving the solvent in oil, unlike vacuum pumps using oil, such as an oil rotary vacuum pump. Consequently, the amount of evaporation of the solvent can be accurately measured and the evaporation pattern of the solvent can be accurately analyzed.

In addition, the use of a gas chromatograph for the measurement allows detection of very low concentration and thus the end point of evaporation (drying) can be easily known.

The vacuum solvent evaporator of the present invention can favorably embody the above-described method for analysis of solvent evaporation patterns.

In particular, a dry diaphragm vacuum pump including at least four diaphragm pump chambers connected in series, each having a diaphragm pump chamber inlet and a diaphragm pump chamber outlet and a gas ballast mechanism provided between the outlet of the third or posterior diaphragm pump chamber upstream from the last diaphragm pump chamber and the inlet of the following diaphragm pump chamber can have a high vacuum ultimate pressure. This pump can reduce the effect of inert gas supply on the ultimate pressure and maintain a stable high-vacuum state.

Thus, even if a practical evaporation is performed in a high vacuum, the evaporation pattern of a solvent can be accurately obtained under conditions close to the conditions for the practical evaporation.

REFERENCE NUMERALS

Figure 1:
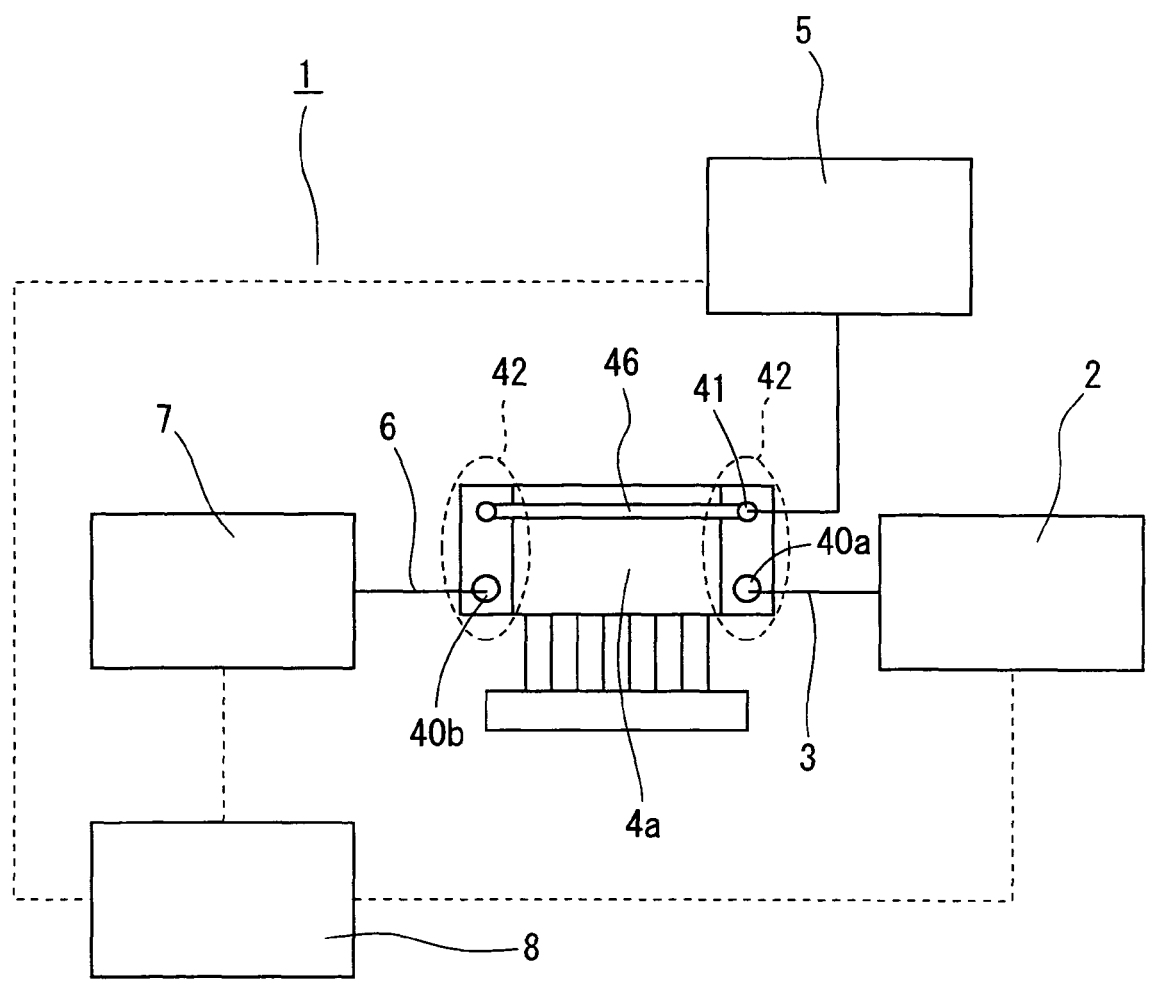
FIG. 1 is a block diagram of a vacuum solvent evaporator according to the present invention.
Figure 2A:
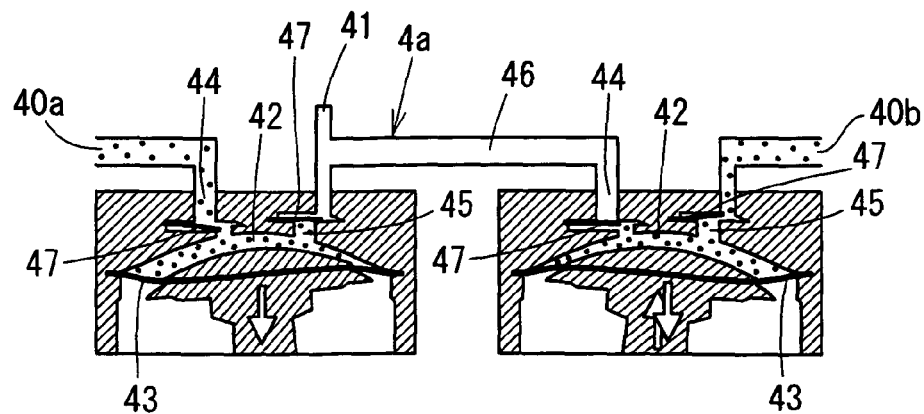
FIG. 2 is a sectional view schematically illustrating the operation of a dry diaphragm vacuum pump of the vacuum solvent evaporator shown in FIG. 1.
Figure 2B:
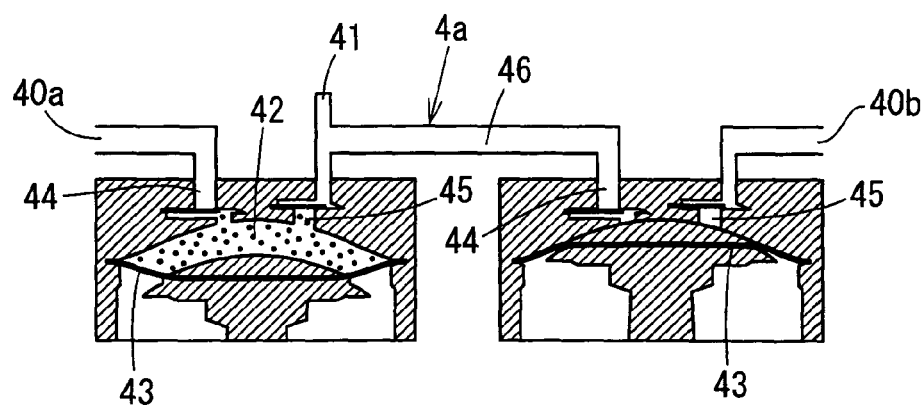
Figure 2C:
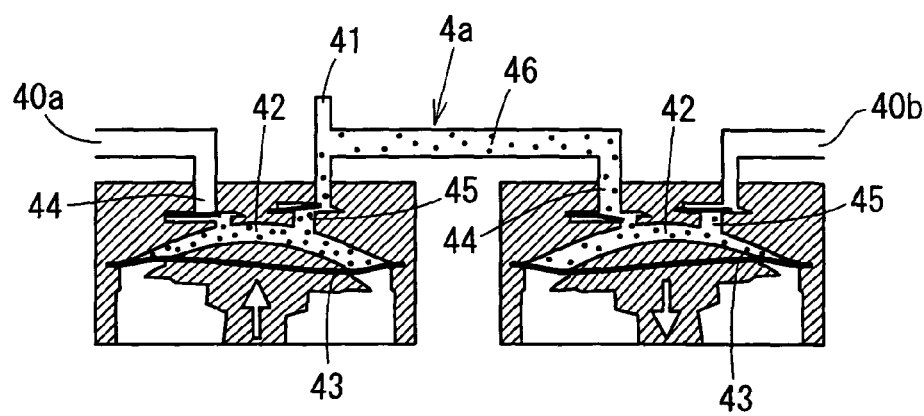
Figure 2D:
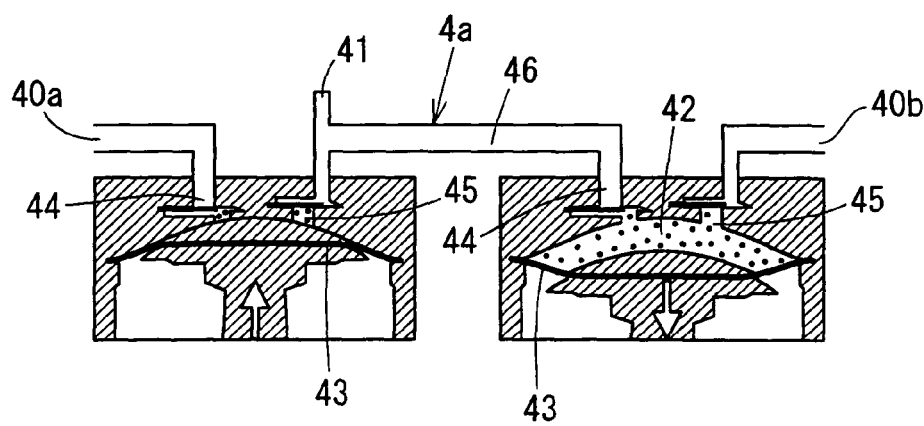

1: vacuum solvent evaporator
2: evaporation means
3: gas intake pipe
4a, 4b: dry diaphragm vacuum pump (evacuation means)
5: inert gas supply means
6: exhaust pipe
7: automatic sampling gas chromatograph (measuring means)
8: personal computer
40a: suction port (suction port of vacuum pump)
40b: exhaust port (exhaust port of vacuum pump)
41: gas ballast mechanism
42: diaphragm pump chamber
43: diaphragm valve
44: diaphragm pump chamber inlet
45: diaphragm pump chamber outlet

BEST MODE FOR CARRYING OUT THE INVENTION

The present invention will now be described in detail with reference to drawings illustrating embodiments of the invention. FIG. 1 shows an example of the vacuum solvent evaporator according to the invention.

As shown in FIG. 1, the vacuum solvent evaporator 1 includes an evaporation means 2, a gas intake pipe 3, a vacuum pump (dry type) 4a serving as evacuation means, inert gas supply means 5, an exhaust pipe 6, an automatic sampling gas chromatograph 7 serving as measuring means, and a personal computer 8.

The evaporation means 2 includes an airtight container (not shown), temperature control means (not shown) for controlling the temperature of an object to be treated in the airtight container, such as a heating device or a cooling device, a temperature sensor for measuring the temperature of the object in the airtight container, and a pressure sensor for measuring the pressure in the airtight container. The temperature measured by the temperature sensor and the pressure measured by the pressure sensor are stored in memory of the personal computer 8.

The airtight container may be changed depending on the conditions of the object to be treated, if necessary, without particular limitation. Exemplary air tight containers include recovery flasks and dryer type models.

The gas intake pipe 3 links the airtight container acting as the evaporation means 2 to the suction port 40a of the vacuum pump 4a, and may be provided with means for controlling the suction speed of the vacuum pump 4a (for example, needle valve or the like) at a point of the length, if necessary.

The vacuum pump 4a draws a solvent gas in the airtight container through the gas intake pipe 3, and discharges the solvent gas from its exhaust port 40b to the exhaust pipe 6 being an exhaust path. The vacuum pump also has two diaphragm pump chambers 42, as shown in FIG. 2.

The two diaphragm pump chambers 42 each include a diaphragm valve 43, a diaphragm pump chamber inlet 44, and a diaphragm pump chamber outlet 45. The diaphragm pump chamber outlet 45 of the first diaphragm pump chamber 42 (upstream chamber, on the left of FIG. 2) is connected to the diaphragm pump chamber inlet 44 of the second diaphragm pump chamber 42 (downstream chamber, on the right of FIG. 2) with a joint pipe 46 made of tetrafluoroethylene resin or the like.

The joint pipe 46 is provided with a gas ballast mechanism (gas ballast valve) 41 near the diaphragm pump chamber outlet 45 of the first diaphragm pump chamber 42.

In FIG. 2, reference numeral 47 designates a check valve provided at the diaphragm pump chamber inlet 44 or the diaphragm pump chamber outlet 45.

How the vacuum pump 4a operates will now be described with reference to FIG. 2.

In the vacuum pump 4a, the diaphragm valves 43 of the two diaphragm pump chambers 42 repeat a series of the operations described in the following (1) to (4), thereby drawing and discharging gas.

(1) As soon as the diaphragm valve 43 of the first diaphragm pump chamber 42 starts drawing gas, the diaphragm valve 43 of the second diaphragm pump chamber 42 starts discharging the gas, as shown in FIG. 2(*a*).

(2) Turning to FIG. 2(*b*), on completion of the drawing operation of the diaphragm valve 43 of the first diaphragm pump chamber 42, the diaphragm valve 43 of the second diaphragm pump chamber 42 completes the discharge.

(3) Turning to FIG. 2(*c*), as soon as the diaphragm valve 43 of the first diaphragm pump chamber 42 starts discharging the gas, the diaphragm valve 43 of the second diaphragm pump chamber 42 starts drawing the gas.

(4) Turning to FIG. 2(*d*), on completion of the discharge operation of the diaphragm valve 43 of the first diaphragm pump chamber 42, the diaphragm valve 43 of the second diaphragm pump chamber 42 completes the drawing.

The inert gas supply means 5 supplies an inert gas to the inside of the vacuum pump 4*a* through the gas ballast mechanism 41 of the vacuum pump 4*a*, for the solvent evaporated from the object in the airtight container, and measures the amount of the supplied inert gas. The measurement result is stored in the memory of the personal computer 8, or inert gas supply amount storage means.

Specifically, the solvent gas drawn from the airtight container by the vacuum pump 4*a* is diluted with the inert gas supplied from the inert gas supply means 5 through the gas ballast mechanism 41 to such a concentration as can be measured by the below-described automatic sampling gas chromatograph 7 without condensation in the exhaust pipe 6.

The means for measuring the amount of inert gas supply is not particularly limited, and a generally used gas flowmeter may be used.

The exhaust pipe 6, which is connected to the exhaust port 40*b* of the vacuum pump 4*a*, discharges exhaust gas containing the drawn solvent gas, or containing the solvent gas and the inert gas for diluting the solvent gas supplied from the inert gas supply means 5.

The automatic sampling gas chromatograph 7, which is connected to the exhaust pipe 6, automatically samples the exhaust gas flowing in the exhaust pipe 6 at predetermined time intervals, and separates and measures the components of the solvent in the sampled gas. A commercially available one (produced by, for example, Aligent Technologies) may be used.

In the personal computer 8, the arithmetic operation means, such as CPU, calculates the concentrations of the components of the solvent in the sample gas, using the peak areas of the response curves for the components of the solvent, obtained from the measurement by the automatic sampling gas chromatograph 7 and stored in the memory, and previously prepared calibration curves. The results of the arithmetic operation are stored in the memory of the personal computer 8, or concentration data storage means.

The personal computer 8 includes an arithmetic operation program for calculating the evaporation patterns of the constituent solvents after completion of the measurement, using the data stored in the memory, such as measured concentration and amount of inert gas supply, and optionally temperature measured by the temperature sensor and pressure measured by the pressure sensor.

A method for analysis of evaporation patterns of solvents with the vacuum solvent evaporator 1 according to the present invention will now be described in detail.

In this method, first, a heating temperature is set for an object to be treated and calibration curves are prepared.

The heating temperature is controlled to a level at which the object is evaporated, with temperature control means, such as a heating bath.

The calibration curves are prepared for the respective constituent solvents in the object by measuring samples whose concentrations have been known with the automatic sampling gas chromatograph 7.

The inert gas is controlled with a valve or the like so as to be supplied at a predetermined flow rate to the inside of the vacuum pump 4 from the inert gas supply means 5. Then, the vacuum pump 4 is brought into operation to start vacuum evaporation of a multicomponent solvent or wet crystal to be dried placed in the airtight container, which is an object to be treated whose weight and solvent content have been measured.

Then, the automatic sampling gas chromatograph 7 automatically samples exhaust gas at predetermined time intervals, and separates and measures the components of the solvent for each sampled gas. The measurement results and the concentrations of the constituent solvents derived from the calibration curves are stored in the memory of the personal computer 8. If the concentrations of the constituent solvents obtained from the measurements of the automatic sampling gas chromatograph 7 are more than or equal to their saturated concentrations, the amount of inert gas supply from the inert gas supply means 5 is increased by adjusting valves.

On completion of the vacuum evaporation, the weight of the residue remaining in the airtight container is measured. Part of the residue is sampled and the content of the solvent remaining in the residue is measured to calculate the amount of the solvent evaporated. The results are stored in the memory of the personal computer 8.

The personal computer 8 stores in the memory the data transmitted from the automatic sampling gas chromatograph 7, such as the sampling time for each sample gas and the concentration of each constituent solvent in the sampled gas, and the data transmitted from the inert gas supply means 5, such as the amount of inert gas supply for each sampling and the weights and solvent contents of the object before and after vacuum evaporation. Also, the CPU, or the arithmetic operation means, prepares graphs of the changes in concentration and evaporation rate with time for each constituent solvent from the data, using separately prepared processing software, and calculates the recovery factor of the automatic sampling gas chromatograph 7 for each evaporated constituent solvent.

Evaporation patterns are thus analyzed under a variety of evaporation conditions, and optimal evaporation conditions are determined from the results of the analyses. The solvent used in practical manufacture can be subjected to vacuum evaporation or vacuum drying under the determined optimal evaporation conditions.

Thus, the vacuum evaporator 1 does not break a vacuum and allows the pressure to be more stable than in the known methods so as not to be affected even by frequent sampling. Consequently, in-depth data can be obtained.

Also, the use of the automatic sampling gas chromatograph can reduce the time for analysis in comparison with manual analysis.

Figure 3:
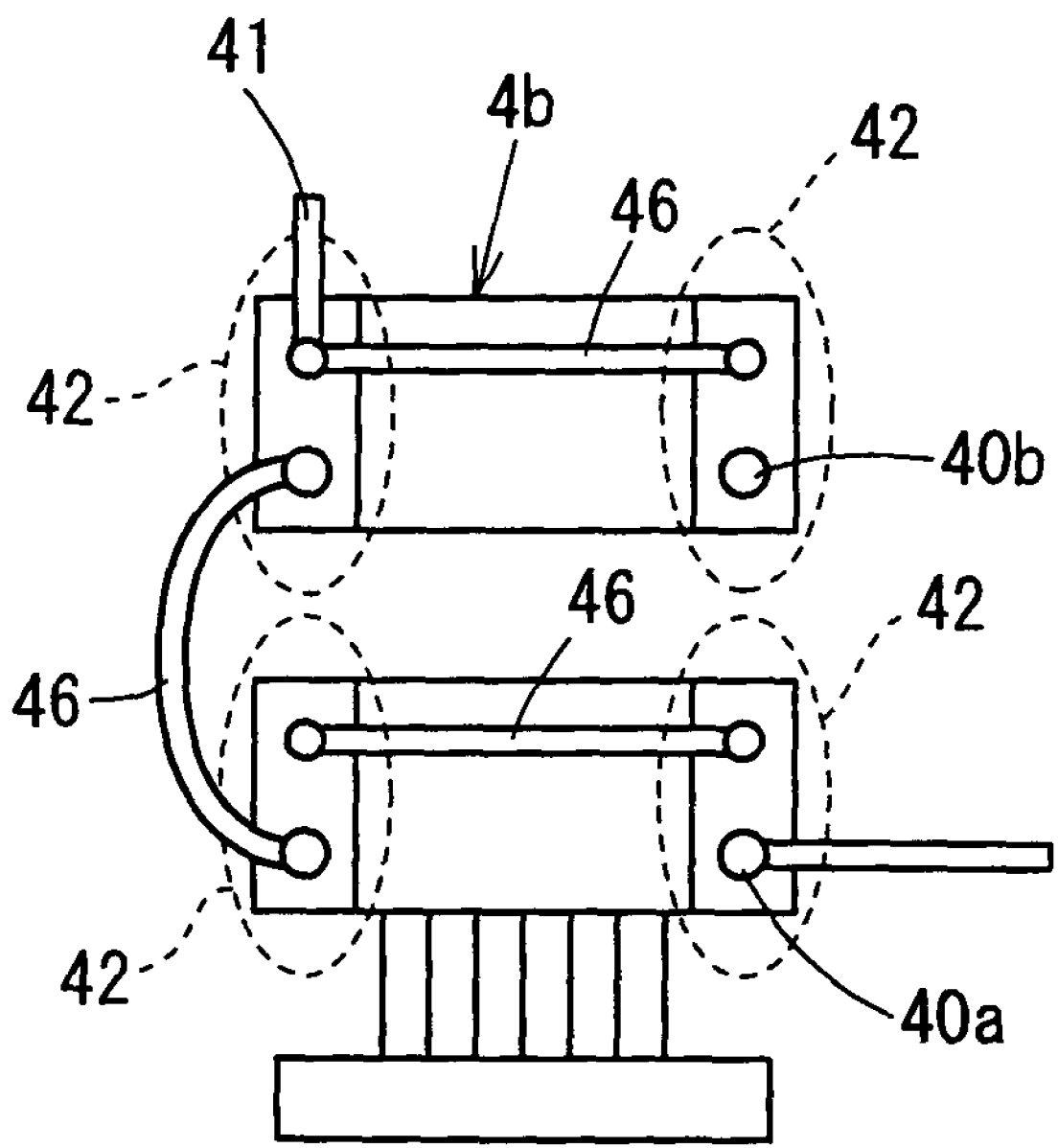
FIG. 3 is a schematic illustration of another dry diaphragm vacuum pump of the vacuum solvent evaporator according to the present invention.
Figure 4:
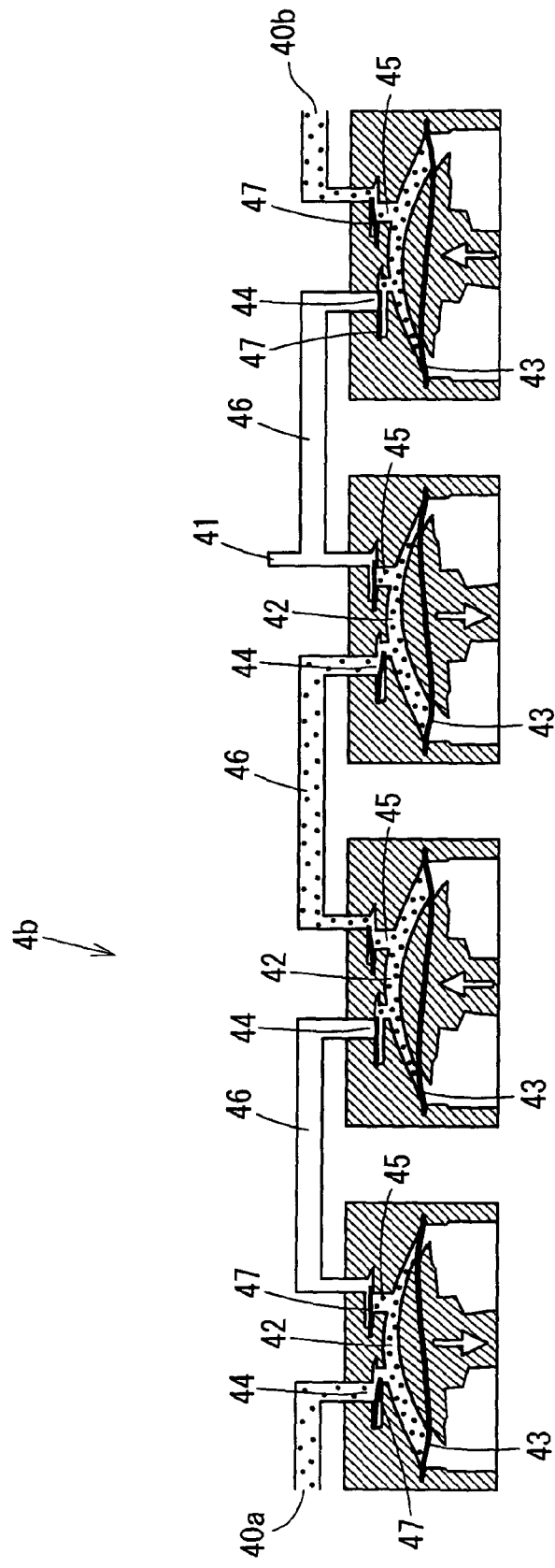
FIG. 4 is a schematic sectional view of the dry diaphragm vacuum pump shown in FIG. 3.

FIGS. 3 and 4 show another example of the vacuum pump used in the vacuum solvent evaporator according to the present invention.

As shown in FIGS. 3 and 4, this vacuum pump 4*b* includes four diaphragm pump chambers 42. The diaphragm pump chamber outlet 45 of the third diaphragm pump chamber 42 (at the third position from the left of FIG. 4) is connected to the diaphragm pump inlet 44 of the fourth one (at the fourth position from the left of FIG. 4) with a joint pipe 46, and a gas ballast mechanism 41 is provided in this joint pipe 46 near the diaphragm pump chamber outlet 45 of the third diaphragm pump chamber 42. The other joint pipes 46 do not have the gas ballast mechanism 41. The other structure is the same as that of the foregoing vacuum pump 4a.

EXAMPLE 1

An IPA aqueous solution (50 g of IPA+50 g of water), which was an object to be treated, was placed in a 0.5 L model dryer being the airtight container of the vacuum solvent evaporator 1. The vacuum solvent evaporator 1 was brought into operation as described above so that the automatic sampling gas chromatograph 7 sampled gas at time intervals of 2 minutes. The concentrations of IPA and water in the sampled gas were thus obtained. The results of the analysis for their evaporation patterns are shown in FIGS. 5 and 6.

Figure 5:
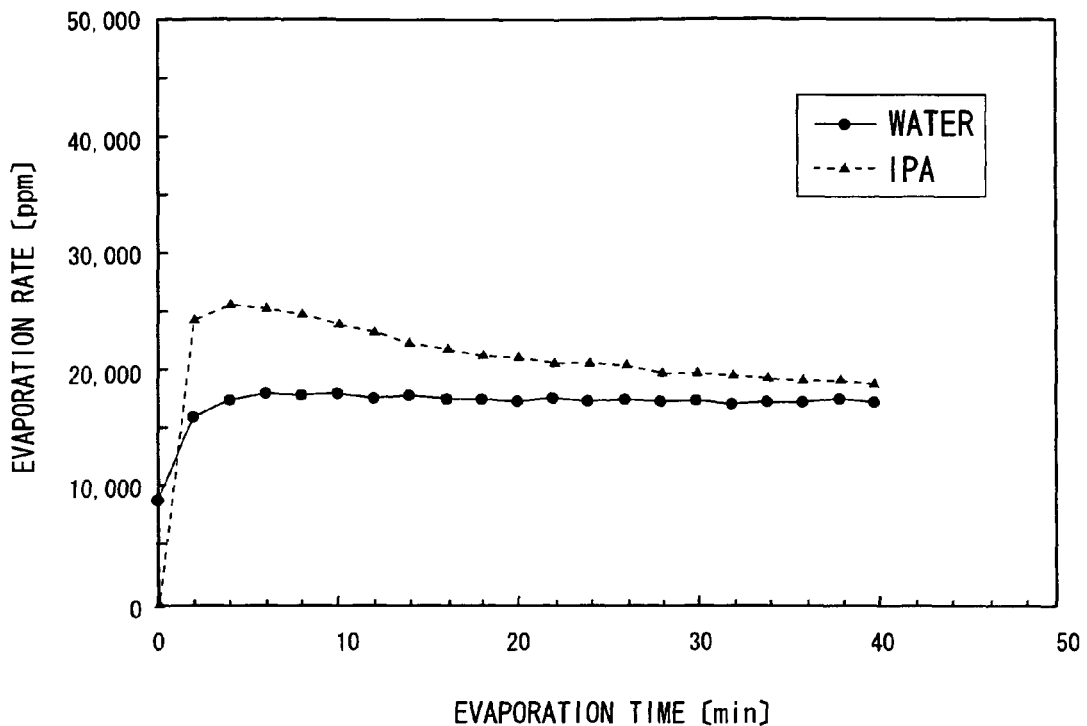
FIG. 5 is a graph of the experimental results in Example 1, showing the changes with time in concentrations of IPA and water of a sample gas evaporated from an IPA aqueous solution.
Figure 6:
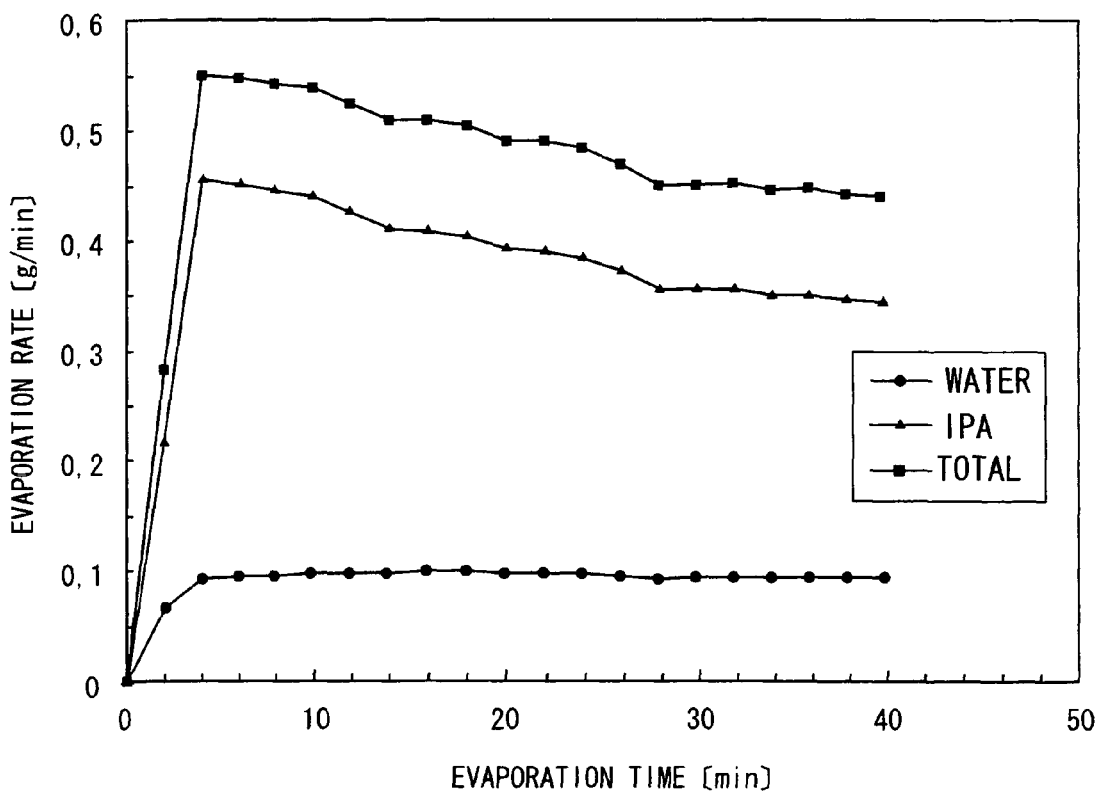
FIG. 6 is a graph of the experimental results in Example 1, showing the changes with time in evaporation rates of IPA and water evaporating from the IPA aqueous solution.

FIG. 5 shows the changes in the concentrations of IPA and water with time, and FIG. 6 shows the changes in the evaporation rates of IPA and water with time. The model dryer was a glass vessel to which a conical dryer used in practical production was miniaturized. The vacuum pump was dry diaphragm vacuum pump A (MZ2C, manufactured by Vacuubrand) including two diaphragm pump chambers connected in series, each having a diaphragm pump chamber inlet and a diaphragm pump chamber outlet, and the gas ballast mechanism provided at the diaphragm pump chamber outlet of the first diaphragm pump chamber, as with the vacuum pump 4a shown in FIG. 2. The exhaust rate was 3 L/min.

Example 1 suggests that the method of the present invention allows short-interval sampling and leads to in-depth data, and that the end point of the evaporation (drying) can be easily known.

EXAMPLE 2

The same vacuum solvent evaporator 1 as in Example 1 was used. An object, 60 g of L-arginine wet crystal (15% by weight of water, 12% by weight of IPA), was placed in a model dryer (the same as in Example 1) being the airtight container, and the vacuum solvent evaporator 1 was brought into operation to obtain the evaporation patterns in the same manner as in Example 1. The results are shown in FIG. 7.

Figure 7:
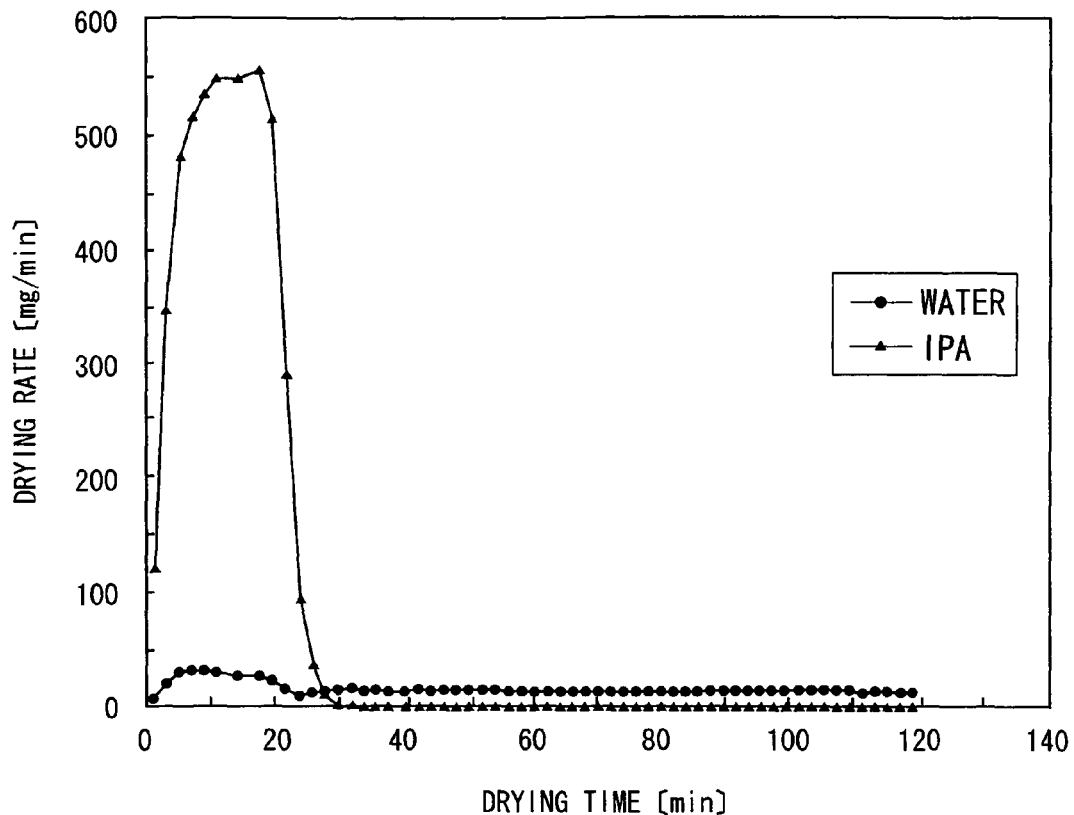
FIG. 7 is a graph of the experimental results in Example 2, showing the changes with time in evaporation rates of IPA and water evaporating from an L-arginine wet crystal.

FIG. 7 shows the changes in the evaporation rates of IPA and water.

Example 2 clearly shows that detailed drying rate curves or other data of a particular object to be dried (hydrate crystal or the like) can be automatically calculated, and that thus various new findings can be obtained.

Also, the vacuum solvent evaporator 1 allowed automatic sampling at time intervals of, in the shortest case, 1 minute, and detection of a trace mount of evaporation as low as 1 mg/min or less. Thus, it has been found that the end point of the evaporation (drying) can be easily known.

EXAMPLE 3

The exhaust rates were measured for vacuum pump A (MZ2C, manufactured by Vacuubrand) used in Example 1 and vacuum pump B (modified from MD4C manufactured by Vacuubrand) including four diaphragm pump chambers connected in series, each having a diaphragm pump chamber inlet and a diaphragm pump chamber outlet, and a gas ballast mechanism provided at the diaphragm pump chamber outlet of the third diaphragm pump chamber. The exhaust rate curves of each vacuum pump was investigated with the needle valve between the vacuum pump and the airtight container adjusted to an opening of 0.72 (needle valve/full open=9 turns/12.5 turns). The results are shown in FIG. 8.

Figure 8:
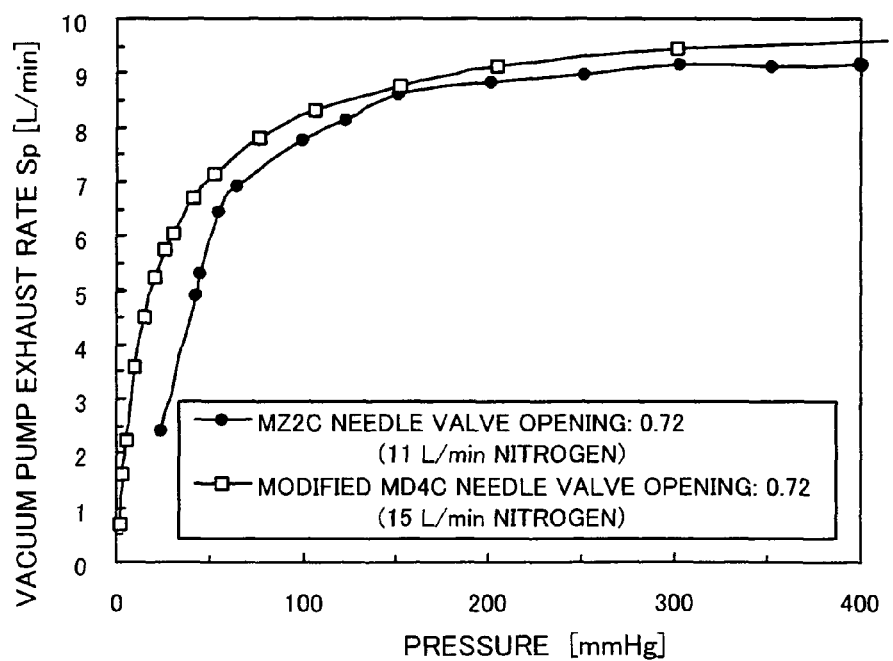
FIG. 8 is a graph for comparison of exhaust rate curves of vacuum pump A and vacuum pump B.

FIG. 8 shows that no large deference is shown between the two pumps when the pressure is increased to 150 mmHg (20 kPa) or more, and that the vacuum pump B has a lower ultimate pressure and accordingly exhibits higher exhaust rate at a pressure close to the ultimate pressure.

EXAMPLE 4

Vacuum pumps B, C, D, and E were prepared: vacuum pump B (modified from MD4C manufactured by Vacuubrand) included four diaphragm pump chambers connected in series, each having a diaphragm pump chamber inlet and a diaphragm pump chamber outlet, and a gas ballast mechanism provided at the diaphragm pump chamber outlet of the third diaphragm pump chamber; vacuum pump C (modified from MD4C manufactured by Vacuubrand) included four diaphragm pump chambers connected in series, each having a diaphragm pump chamber inlet and a diaphragm pump chamber outlet, and a gas ballast mechanism provided at the diaphragm pump chamber outlet of the second diaphragm pump chamber; vacuum pump D (modified from MD4C manufactured by Vacuubrand) included four diaphragm pump chambers connected in series, each having a diaphragm pump chamber inlet and a diaphragm pump chamber outlet, and a gas ballast mechanism provided at the diaphragm pump chamber outlet of the first diaphragm pump chamber; and vacuum pump E (modified from MD4C manufactured by Vacuubrand) included four diaphragm pump chambers connected in series, each having a diaphragm pump chamber inlet and a diaphragm pump chamber outlet, but no gas ballast mechanism. Then, the suction port of each vacuum pump was directly connected to the exhaust port of a 20 L stainless steel can with no needle valve. How the position from which nitrogen is introduced (position of the gas ballast) affects the exhaust rate and the ultimate pressure was investigated by an air decompression technique measuring the changes in internal pressure of the stainless steel can with time. The results are shown in Table 1. In vacuum pumps B to D, the gas ballast mechanism supplied nitrogen at a speed of 15 L/min.

TABLE 1

|  | Maximum exhaust rate (L/min) | Ultimate pressure (mmHg) | Nitrogen supply |
| --- | --- | --- | --- |
| Vacuum pump B | 32 | 4.7 | 15 L/min |
| Vacuum pump C | 29 | 10 | 15 L/min |
| Vacuum pump D | 29 | 32 | 15 L/min |
| Vacuum pump E | 33 | 3.6 | 0 |

Table 1 shows that as the inert gas supply is positioned more downstream, the effect of nitrogen introduction on the ultimate pressure is reduced.

The present invention is not limited to the above described Examples. While in the Examples, appropriate conditions for vacuum evaporation using the vacuum solvent evaporator 1 are determined in advance through experiments and then practical production is performed according to the results, the invention can be used for monitoring of a vacuum evaporation step in practical production. For example, an evaporation dryer used in practical production may be provided with a bypass in its vacuum line and the solvent gas from an object is conducted to the vacuum pump of the present invention through the bypass. The gas is treated in the same manner as in the present invention and then sampled to be analyzed with an automatic sampling gas chromatograph.

While in the Examples, data of the automatic sampling gas chromatography are directly input to the personal computer, the data of the automatic sampling gas chromatography may be stored in a recording medium, such as a flexible disk, and the data in the recording medium may be analyzed by software of another personal computer.

While the Examples use the automatic sampling gas chromatograph, sampling may be manually performed at predetermined time intervals and the sampled gas may be measured separately with a gas chromatograph.

While in the Examples, exhaust gas of the drawn solvent gas diluted with an inert gas is measured with an automatic sampling gas chromatograph, the exhaust gas may be measured as it is with the automatic sampling gas chromatograph without diluting with an inert gas if the solvent concentration of the drawn solvent gas is low.

INDUSTRIAL APPLICABILITY

The method for analysis of solvent evaporation patterns according to the present invention and the vacuum solvent evaporator capable of embodying the method can be applied to removal of solvents from chemical substances, such as medical drugs, drying of chemical substances, drying of washed workpieces of: electric and electronic devices, such as print boards and hard disks; devices for automobile, machinery, and metal industries, such as brake components and electrical components; precision and optical devices, such as camera components and clock components, drying of food and farm products, and monitoring for progress of drying of inorganic materials, such as metal powder, and residual solvents.

The invention claimed is:

1. A vacuum solvent evaporator comprising:
   an airtight container for housing an object containing a single-component or multicomponent solvent;
   a dry diaphragm vacuum pump including a suction port from which a gas of the solvent evaporated in the airtight container is drawn, an exhaust port from which the gas is discharged;
   a gas ballast mechanism serving as an inert gas supply port; and
   at least four diaphragm pump chambers connected in series, each having a diaphragm pump chamber inlet through which gas is drawn and a diaphragm pump chamber outlet from which the gas is discharged, wherein the gas ballast mechanism is disposed between the outlet of the third or posterior diaphragm pump chamber upstream from the last diaphragm pump chamber and the inlet of the following diaphragm pump chamber; and
   further wherein the gas ballast mechanism disposed between the outlet of the third or posterior diaphragm pump chamber upstream from the last diaphragm pump chamber and the inlet of the following diaphragm pump chamber is the only gas ballast mechanism disposed between the diaphragm pump chambers;
   and an inert gas supply port through which an inert gas is supplied from the outside to the solvent gas drawn into the vacuum pump;
   inert gas supply means for supplying the inert gas into the vacuum pump through the inert gas supply port while the amount of gas supply is measured, thereby diluting the drawn solvent gas;
   inert gas supply amount storage means for storing the amount of inert gas supply measured by the inert gas supply means;
   a gas chromatograph for automatically sampling the gas discharged from the exhaust port of the vacuum pump at predetermined time intervals and measuring the solvent gas in the sampled gas;
   arithmetic operation means for calculating the concentration of the solvent gas from the measurement results of the gas chromatograph and a previously prepared calibration curve; and
   concentration data storage means for storing the solvent gas concentration obtained by the arithmetic operation means.

2. The vacuum solvent evaporator according to claim 1, further comprising:
   a temperature control means for controlling the temperature of the object in the airtight container.

3. The vacuum solvent evaporator according to claim 1, further comprising:
   a pressure sensor means for measuring the pressure in the airtight container.

4. A vacuum solvent evaporator, comprising:
   an airtight container to house an object containing a single-component or multi-component solvent;
   a gas ballast mechanism inert gas supply port; and
   a dry diaphragm vacuum pump comprising at least four diaphragm chambers, a suction port and an exhaust port, wherein the suction port is connected to the airtight container and the dry diaphragm vacuum pump draws the solvent from the airtight container through the suction port, wherein the four diaphragm pump chambers are connected sequentially in series and each diaphragm pump chamber has an inlet through which gas is drawn and an outlet through which gas is discharged, and wherein the gas ballast mechanism inert gas supply port is disposed between an outlet of the third or posterior diaphragm pump chamber upstream from the last diaphragm pump chamber and the inlet of the following diaphragm pump chamber; and
   further wherein the gas ballast mechanism disposed between the outlet of the third or posterior diaphragm pump chamber upstream from the last diaphragm pump chamber and the inlet of the following diaphragm pump chamber is the only gas ballast mechanism disposed between the diaphragm pump chambers;
   an inert gas supply to supply an inert gas to the vacuum pump through the gas ballast mechanism inert gas supply port;
   an inert gas supply storage to store an amount of the inert gas;
   a gas chromatograph to sample the gas discharged from the exhaust port of the vacuum pump and to measure the amount of the solvent in the gas discharged from the exhaust port of the vacuum pump;
   an arithmetic calculator to calculate the concentration of the solvent from the gas chromatograph and a calibration curve; and
   a concentration data store to store the solvent gas concentration calculations of the arithmetic calculator.

5. The vacuum solvent evaporator according to claim 4, further comprising:
   a temperature controller to controlling the temperature of the object in the airtight container.

6. The vacuum solvent evaporator according to claim 4, further comprising:

a pressure sensor to measure the pressure in the airtight container.

7. The vacuum solvent evaporator according to claim 1, wherein the gas ballast mechanism is disposed between the outlet of the third diaphragm pump chamber and the fourth diaphragm pump chamber.

8. The vacuum solvent evaporator according to claim 4, wherein the gas ballast mechanism is disposed between the outlet of the third diaphragm pump chamber and the fourth diaphragm pump chamber.

* * * * *